United States Patent [19]

Tsuboi et al.

[11] Patent Number: 4,731,385
[45] Date of Patent: Mar. 15, 1988

[54] INSECTICIDAL AND FUNGICIDAL COMPOSITION FOR AGRICULTURAL AND HORTICULTURAL USE

[75] Inventors: Shinichi Tsuboi; Shoko Sasaki, both of Hino; Yumi Hattori; Yoshio Kurahashi, both of Hachioji; Shinji Sakawa, Hino; Toshihito Kondo, Hachioji, all of Japan

[73] Assignee: Nihon Tokushu Noyaku Seizo K.K., Tokyo, Japan

[21] Appl. No.: 921,294

[22] Filed: Oct. 21, 1986

[30] Foreign Application Priority Data

| Oct. 26, 1985 | [JP] | Japan | 60-240237 |
| Oct. 26, 1985 | [JP] | Japan | 60-240238 |
| Oct. 26, 1985 | [JP] | Japan | 60-240239 |
| Oct. 26, 1985 | [JP] | Japan | 60-240240 |
| Oct. 26, 1985 | [JP] | Japan | 60-240241 |

[51] Int. Cl.$^4$ ............... A61K 31/00; A61K 45/00
[52] U.S. Cl. .................... 514/789; 514/130; 514/470; 514/585; 514/617; 514/294; 514/367; 514/146; 514/247; 514/341
[58] Field of Search ........................... 514/789

[56] References Cited

U.S. PATENT DOCUMENTS

| 3,629,411 | 12/1971 | Schrader et al. | 514/130 |
| 3,629,428 | 12/1971 | Seki et al. | 514/367 |
| 3,663,704 | 5/1972 | Aoki et al. | 514/470 |
| 3,937,840 | 2/1976 | Chiyomaru et al. | 514/617 |
| 3,985,804 | 10/1976 | Chiyomaru et al. | 564/184 |
| 4,008,325 | 2/1977 | Bass et al. | 514/294 |
| 4,052,395 | 10/1977 | Jojima et al. | 514/247 |
| 4,093,743 | 6/1978 | Yabutani et al. | 514/617 |
| 4,127,673 | 11/1978 | Yamada et al. | 514/585 |
| 4,647,570 | 3/1987 | Shiokawa et al. | 514/341 |
| 4,678,795 | 7/1987 | Shiokawa et al. | 514/341 |

FOREIGN PATENT DOCUMENTS 1419122 12/1975 United Kingdom .

Primary Examiner—John E. Kittle
Assistant Examiner—Susan S. Rucker
Attorney, Agent, or Firm—Sprung Horn Kramer & Woods

[57] ABSTRACT

An insecticidal and fungicidal composition comprising (1) An insecticidally effective amount of a nitromethylene derivative of the formula

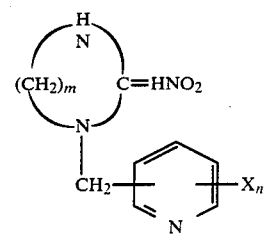

in which
X is a lower alkyl group, a lower alkoxy group, or a halogen atom,
n is 0, 1 or 2 and
m is 2 or 3, and a fungicidally effective amount of at least one fungicide selected from the group consisting of
(2) O-ethyl S,S-diphenyl phosphorodithioate,
(3) 4,5,6,7-tetrachlorophthalide,
(4) 1-(4-chlorobenzyl)-1-cyclopentyl-3-phenylurea,
(5) Validamycin A, 3'-iso-propoxy-2-methylbenzenilide, o-trifluoromethyl-m'-isopropoxybenzoylanilide or 6-(3,5-dichloro-4-methylphenyl-3(2H)pyridazinone, and
(6) di-isopropyl-1,3-dithiolan-2-ylidenemalonate, 5-methyl-1,2,4-triazo[3,4-b]-benzothiazole, 3-allyloxy-1,2-benzisothiazole 1,1-dioxide, and 1,2,5,6-tetrahydro-4H-pyrrolo-[3,2,1-i,j]quinolin-4-one, [5-amino-2-methyl-6-(2,3,4,5,6-pentahydroxycyclohexyloxy)tetrahydropyran-3-yl]amino-α-iminoacetic acid or S-benzyl diisopropylphosphorothiolate.

7 Claims, No Drawings

INSECTICIDAL AND FUNGICIDAL COMPOSITION FOR AGRICULTURAL AND HORTICULTURAL USE

The present invention relates to novel insecticidal and fungicidal synergistic combinations of known nitromethylene derivatives and known fungicides.

Nitromethylene derivatives and their use as an insecticide have already been disclosed (see Japanese Patent Applications Nos. 72966/1984 and 132943/1984, corresponding to U.S. Application Ser. No. 720,838, filed Apr. 8, 1985 U.S. Pat. No. 4,678,795, and Japanese Laid Open Patent Application No. 172976/1985, corresponding to U.S. Application Ser. No. 699,756, filed Feb. 8, 1985 U.S. Pat. No. 4,647,570).

It has already been disclosed that O-ethyl S,S-diphenyl phosphorodithioate has an activity of controlling rice blast (Pyricularia oryzae) (See Japanese Patent Publication No. 12919/1969, corresponding to U.S. Pat. No. 3,629,411).

It has furthermore already been disclosed that 4,5,6,7-tetrachlorophthalide has an activity of controlling rice blast (Pyricularia oryzae) (see Japanese Patent Publication No. 32592/1969, corresponding to U.S. Pat. No. 3,663,704).

It has furthermore been disclosed that 1-(4-chlorobenzyl)-1-cyclopentyl-3-phenylurea has an activity of controlling diseases of agricultural and horticultural crops. (See Japanese Patent Publ No. 50014/1980, corresponding to U.S. Pat. No. 4,127,673).

It has furthermore been disclosed that the following compounds have fungicidal activity for agriculture and horticulture; Validamycin A (see the Pesticide Manual, 7th edition, 1983 published by the British Crop Protection Council), 3'-iso-propoxy-2-methylbenzanilide (see Japanese Patent Publication No. 37048/1977, corresponding to U.S. Pat. Nos. 3,937,840 and 3,985,804), o-trifluoromethyl-m'-isopropoxybenzoylanilide (see Japanese Patent Publication No. 45907/1981, corresponding to U.S. Pat. No. 4,093,743) and 6-(3,5-dichloro-4-methylphenyl)-3-(2H)pyridazinone (see Japanese Laid Open Patent Application No. 34928/1977, corresponding to U.S. Pat. No. 4,052,395).

It has furthermore been disclosed that the following compounds have fungicidal activity against rice blast (Pyricularia oryzae): di-isopropyl 1,3-dithiolan-2-ylidenemalonate (see Japanese Patent Publication No. 34126/1972), 5-methyl-1,2,4-triazolo[3,4-b]benzothiazole (see Japanese Patent Publication No. 18338/1979, corresponding to British Pat. No. 1,419,122), 3-allyl-oxy-1,2-benzisothiazole-1,1-dioxide (see Japanese Patent Publication No. 38080/1970, corresponding to U.S. Pat. No. 3,629,428) and 1,2,5,6-tetrahydro-4H-pyrrolo-[3,2,1-i,j]quinolin-4-one (see Japanese Patent Publication No. 48176/1977, corresponding to U.S. Pat. No. 4,008,325).

However, the activities of the above mentioned nitromethylenes and fungicidal compounds are not entirely satisfactory especially when the concentrations of these active compounds are low and when they are used only in small amounts.

These active compounds show either an insecticidal effect or a fungicidal effect when used singly and cannot simultaneously control diseases caused by pathogens, and damage caused by insects.

It has been found that novel active substance combinations of (1) a nitromethylene derivative of the general formula

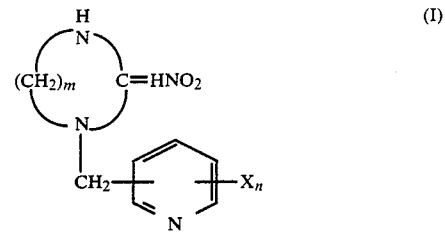

wherein

X represents a lower alkyl group, a lower alkoxy group, or a halogen atom, n represents 0, 1 or 2, and m represents 2 or 3, and at least one fungicidal compound selected from one of the following groups (2) to (6):

(2) O-ethyl S,S-diphenyl phosphorodithioate, (common name: edifenphos)

(3) 4,5,6,7-tetrachlorophthalide, (common name: phthalide)

(4) 1-(4-chlorobenzyl)-1-cyclopentyl-3-phenylurea, (common name: pencycuron)

(5) group of compounds selected from Validamycin A, 3'-iso-propoxy-2-methylbenzanilide, (common name: mepronil), o-trifluoromethyl-m'-isopropoxybenzoylanilide (common name: flutolanil) and 6-(3,5-dichloro-4-methylphenyl)-3(2H)pyridazinone, (6) group of compounds selected from di-isopropyl 1,3-dithiolan-2-ylidenemalonate (common name: isoprothiolane), 5-methyl-1,2,4-triazo[3,4-b]-benzothiazole (common name: tricylcazole), 3-allyloxy-1,2-benzisothiazole 1,1-dioxide (common name: probenazole), and 1,2,5,6-tetrahydro-4H-pyrrolo-[3,2,1-i,j]quinolin-4-one (common name: pyroquilon), [5-amino-2-methyl-6-(2,3,4,5,6-pentahydroxycyclohexyloxy)tetrahydropyran-3-yl)amino-α-iminoacetic acid, S-benzyl diisopropylphosphorothiolate, exhibit particular high insecticidal and fungicidal activities.

Surprisingly, the activity of the active substance combinations according to the invention is substantially greater than the sum of the effects of the individual active substances. Accordingly, a genuine synergistic effect is present. And further the active substance combinations according to the invention exhibit simultaneously excellent insecticidal and fungicidal effects against insects and diseases on agricultural crops.

Accordingly, the insecticidal and fungicidal composition of this invention is very effective for the simultaneous control of diseases and insects and saving of labor in the cultivation of agricultural crops, and provides a very outstanding technical advance in industrial utility.

The nitromethylene derivatives of general formula (I) used in the active substance combinations according to the invention are defined by the following formula

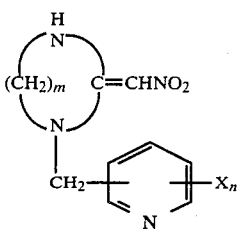

wherein
X represents a lower alkyl group, a lower alkoxy group, or a halogen atom,
n represents 0, 1 or 2, and
m represents 2 or 3.

In formula (I), preferably, X represents a methyl group, a methoxy group, a chlorine atom, a bromine atom or a fluorine atom, n represents 1 or 2, m represents 2 or 3, and the bonding position on the pyridine ring is 3- (or 5-).

The nitromethylene derivatives of general formula (I) can exist also in the form of salts. Examples of the salts include inorganic acid salts, sulfonic acid salts, organic acid salts and metal salts, preferably hydrochlorides, p-toluenesulfonates, cupric acetates, and succinates. Accordingly, the nitromethylene derivatives of formula (I), as used herein, denote their salts as well.

Examples of the nitromethylene derivatives of general formula (I) used in active substance combinations according to the invention include 1-(3-pyridylmethyl)-2-(nitromethylene)tetrahydropyrimidine,
1-(2-methyl-5-pyridylmethyl)-2-(nitromethylene)imidiazolidine,
1-(2-methyl-5-pyridylmethyl)-2-(nitromethylene)tetrahydropyrimidine,
1-(2-methoxy-5-pyridylmethyl)-2-(nitromethylene)imidazolidine,
1-(2-methoxy-5-pyridylmethyl)-2-(nitromethylene)tetrahydropyrimidine,
1-(2-chloro-5-pyridylmethyl)-2-(nitromethylene)imidazolidine,
1-(2-chloro-5-pyridylmethyl)-2-(nitromethylene)tetrahydropyrimidine,
1-(2-fluoro-5-pyridylmethyl)-2-(nitromethylene)imidazoline,
1-(2-fluoro-5-pyridylmethyl)-2-(nitromethylene)tetrahydropyrimidine,
1-(2-bromo-5-pyridylmethyl)-2-(nitromethylene)imidazolidine,
1-(2-bromo-5-pyridylmethyl)-2-(nitromethylene)tetrahydropyrimidine,
1-(5-chloro-2-pyridylmethyl)-2-(nitromethylene)imidazolidine,
1-(5-chloro-2-pyridylmethyl)-2-(nitromethylene)tetrahydropyrimidine,
1-(2,4-dichloro-5-pyridylmethyl)-2-(nitromethylene)tetrahydropyrimidine,
1-(2,4-dibromo-5-pyridylmethyl)-2-(nitromethylene)imidazolidine,
1-(2,3-dichloro-5-pyridylmethyl)-2-(nitromethylene)imidazolidine,
1-(3-pyridylmethyl)-2-(nitromethylene)tetrahydropyrimidine hydrochloride,
1-(2-methyl-5-pyridylmethyl)-2-(nitromethylene)tetrahydropyrimidine p-toluenesulfonate,
1-(2-methoxy-5-pyridylmethyl)-2-(nitromethylene)tetrahydropyrimidine succinate,
1-(2-chloro-5-pyridylmethyl)-2-(nitromethylene)imidazolidine hydrochloride,
1-(2-fluoro-5-pyridylmethyl)-2-(nitromethylene)tetrahydropyrimidine cupric acetate,
1-(2-bromo-5-pyridylmethyl)-2-(nitromethylene)imidazolidine succinate, and
1-(2,4-dichloro-5-pyridylmethyl)-2-(nitromethylene)tetrahydropyrimidine p-toluenesulfonate.

The insecticidal activity of the nitromethylene derivatives of general formula (I) is described in Japanese Patent Application Nos. 26020/1984, 72966/1984 and 132943/1984.

O-Ethyl S,S-diphenyl phosphorodithioate (edifenphos), component of group (2) of the active substance combinations according to the invention, is already known as a rice blast controlling agent (see Japanese Patent Publication No. 12919/1969). The 4,5,6,7-tetrachlorophthalide (phthalide), the component of group (3) is also known as rice blast controlling agent (see Japanese Patent Publication No. 32592/1969).

1-(4-Chlorobenzyl)-1-cyclopentyl-3-phenylurea (pencycuron), component (4) of the active substance combinations according to the invention, is already known as an agricultural and horticultural fungicide (see Japanese Patent Publication No. 50014/1980, supra).

Agricultural-horticultural fungicidal compounds belonging to group (5) and used in the active substance combinations according to the invention are shown by the following formulae:

3'-isopropoxy-2-methylbenzanilide (mepronil)
(Japanese Patent Publication No. 37048/1977, supra)

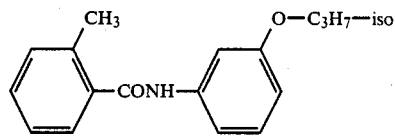

o-trifluoromethyl-m'-isopropoxybenzoylanilide (flutolanil) (Japanese Patent Publication No. 45907/1981, supra)

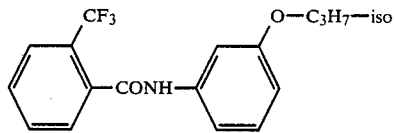

6-(3,5-dichloro-4-methylphenyl)-3(2H)pyridazinone (Japanese Laid Open Patent Application No. 34928/1977, supra).

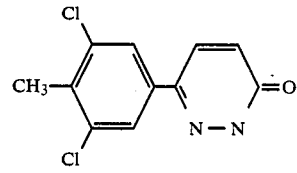

The fungicidally active compounds of group (6) used in the active substance combinations according to the invention are shown by the following formulae:

di-isopropyl 1,3-dithiolan-2-ylidenemalonate (isoprothiolane) (see Japanese Patent Publication No. 34126/1972)

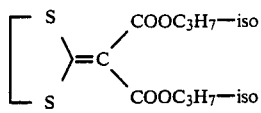

5-methyl-1,2,4-triazolo[3,4-b]benzothiazole(tricyclazole) (see Japanese Patent Publication No. 18338/1979, supra)

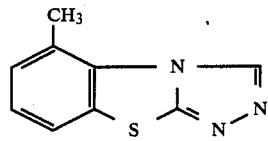

3-allyloxy-1,2-benzoisothiazole 1,1-dioxide(probenazole) (see Japanse Patent Publication No. 38080/1970, supra)

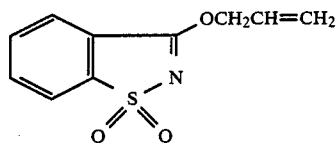

1,2,5,6-tetrahydro-4H-pyrrolo[3,2,1-i,j]quinolin-4-one (pyroquilon) (see Japanese Patent Publication No. 48176/1977, supra)

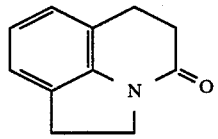

Furthermore, excellent effects can be obtained by using [5-amino-2-methyl-6-(2,3,4,5,6-pentahydroxycyclohexyloxy)tetrahydropyran-3-yl]amino-α-iminoacetic acid and its hydrochloride (kasugamycin) or S-benzyl diisopropylphosphorothiolate (IBP) as members of group (6) compounds.

The weight ratios of the group of active substances in the active substance combinations can vary within relatively wide ranges. In general 0.05 to 20 parts by weight of active substance of the groups (2), (3), (4), (5) and (6) respectively, preferably 0.1 to 10 parts by weight, are used per part by weight of active substance of the group of active substances (1).

The active substance combinations according to the invention shows excellent insecticidal and fungicidal activities, and can be used as an insecticidal and fungicidal agent by, for example, foliar application, underwater or water surface application, soil application, soil mixing treatment or application to a nursury box.

The active substance combinations according to the invention show excellent insecticidal and fungicidal activities and therefore can be used as an insecticidal and fungicidal agent. The active substance combinations according to the invention have no phytotoxicity to cultivated plants and low toxicity to warm-blooded animals, and can be used to accurately control diseases and insects in agriculture, horticulture and forestry, and protection of stored crops and products. They are usually active against sensitive and resistant species, and against all or some stages of growth.

The above-mentioned pests such as insects and diseases include the following examples.

Insect pests

Coleopterous insect
  *Callosobruchus chinensis,*
  *Sitophilus zeamais,*
  *Tribolium castaneum,*
  *Epilachna vigitioctomaculata,*
  *Agriotes fuscicollis,*
  *Anomala rufocuprea,*
  *Leptinotarsa decemkineata,*
  *Diabrotica spp.,*
  *Monochamus alternatus,*
  *Lissorhoptrus oryzophilus,*
  *Echinocinemus squameus,*
  *Oulema oryzae,* and
  *Lyctus bruneus.*

Lepidopterous insects
  *Lymantria dispar,*
  *Malacosoma neustria,*
  *Pieris rapae,*
  *Spodoptera litura,*
  *Mamestra brassicae,*
  *Chilo suppressalis,*
  *Cnaphalocrocis medinalis,*
  *Naranga aenescens,*
  *Pyrausta nubilalis,*
  *Ephestia cautella,*
  *Adoxophyes orana,*
  *Carpocapsa pomonella,*
  *Agrotis fucosa,*
  *Galleria mellonella,*
  *Plutella maculipennis,*
  *Heliothis virescens,*
  *Phyllocnistis citrella,* and
  *Parnara guttata.*

Hemipterous insects
  *Nephotettix cincticeps,*
  *Nilaparvata lugens,*
  *Laodelphax striatelluo,*
  *Sogatella furcifera,*
  *Pseudococcus comstocki,*
  *Unaspis yanonensis,*
  *Myzus persicae,*
  *Aphis pomi,*
  *Aphis gossypii,*
  *Rhopalosiphum pseudobrassicas,*
  *Stephanitis nashi,*
  Nazara spp.,
  *Trialeurodes vaporariorum,* and
  Psylla spp.

Orthopterous insects
  *Gryllotalpa africana,* and
  *Locusta migratoria migratoriodes.*

Plant diseases caused by fungi such as Archiomycetes, Phycomycetes, Ascomycetes, Basidiomycetes and Fungi Imperfecti; and those caused by bacteria.

Typical examples of the fungicidal spectrum of the plant diseases mentioned above include rice blast (*Piricularia oryzae*), *Cochliobolus Miyabeanus,* a kind of pathogen causing withering of rice ears, rice sheath blight (*Pellicularia sasakii*) and *Rhizoctonia solani*, a kind of pathogen causing damping-off to vegetables. These examples however, are not limitative.

The active substance combinations can be converted into the customary formulations, such as solutions, emulsions, suspensions, powders, foams, pastes, granules, aerosols, natural and synthetic materials impregnated with active compound, very find capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active substance combinations with extenders, preferably with liquid or liquefied gaseous or solid diluents or carriers, optionally with the use of surface-active agents, preferably emulsifying agents and/or dispersing agents and/or foam-forming agents. In the case of the use of water as an extender, organic solvents can, for example, also be used as auxiliary solvents.

As liquid solvents, diluents or carriers, there are suitable for example aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers there are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic materials such as sawdust, coconut shells, corn cobs and tabacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulation in general contain from 0.1 to 95 percent by weight of active compound, preferably from 0.5 to 90 percent by weight.

The active substance combinations according to the invention can be present in their commercially available formulations and in the use forms prepared from these formulations, as a mixture with other active compounds, such as insecticides, sterilizing agents, fungicides, growth-regulating substances or herbicides. The insecticides include, for example, phosphates, carbamates, carboxylates, chlorinated hydrocarbons, phenylureas, stances produced by microorganisms.

The active substance combinations according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.00001 to 100% by weight of active compound, preferably between 0.001 and 5% by weight.

The compounds are employed in a customary manner appropriate for the use forms.

The following examples illustrate the present invention more specifically. It should be understood, however, that the invention is in no way limited to these examples alone.

(A) Biological and Formulation Examples relating to novel active substance combinations of (1) a nitromethylene derivative of formula (I) and (2) O-ethyl S,S-diphenylphosphorodithiate, optionally in combination with (3) 4,5,6,7-tetrachlorophthalide.

EXAMPLE 1

(1) Test on brown planthopper (Nilaparvata lugens):
Preparation of test compounds
Each active compound: 25 to 50 parts by weight
Carrier: 45 to 70 parts by weight of a 1:5 mixture of diatomaceous earth and kaolin
Emulsifier: 5 parts by weight of polyoxyethylene alkyl phenyl ether The active compound, the carrier and the emulsifier in the amounts indicated above were pulverized and mixed to form a wettable powder. A predetermined amount of said wettable powder was diluted with water and mixed.

Testing method

Three rice seedlings, 15 cm tall, were planted in pots having a diameter of about 13 cm. Ten days after the planting, a water dilution of the active compounds in a predetermined concentration prepared in advance was sprayed onto the plants at a rate of 20 ml per pot by means of a spray gun. After having air dried the spray, a cage was put over each pot, and ten 4th instar larvae of brown planthopper were inoculated in each pot. Three days later, the number of dead insects was counted, and the kill ratio was calculated.

(2) Test for efficacy on rice blast by foliar application

Testing method

Paddy rice (variety: Asahi) was grown in unglazed pots each having a diameter of 12 cam, and in the 3- to 4-leaf stage, a dilution of the active compounds in a predetermined concentration prepared in advance was sprayed onto the plants at a rate of 50 ml per three pots. The next day, an artificially cultivated suspension of *Piricularia oryzae* spores was inoculated in the plants by spraying it twice. The pots were then maintained in a chamber kept at 25° C. and having a relative humidity of 100% to cause infection. Seven days after the inoculation, the degree of disease per pot was rated and evaluated on the following standard, and the control index (%) was calculated. The phytotoxicity to the plants was also examined.

| Degree of disease | Percentage of the area of lesions |
|---|---|
| 0 | 0 |
| 0.5 | 2 or less |
| 1 | 3–5 |
| 2 | 6–10 |
| 3 | 11–20 |
| 4 | 21–40 |
| 5 | 41 or more |

$$\text{Control index (\%)} = \frac{\text{Degree of disease in the non-treated area} - \text{Degree of disease in the treated area}}{\text{Degree of disease in the non-treated area}} \times 100$$

In the present tests, one test area consisted of three pots.

The results of the test (1) and (2) are summarized in Table 1.

TABLE 1

| Test chemical | Concentrations of the active ingredients (ppm) | Brown plant-hopper Kill ratio (%) | Rice blast Control index (%) |
|---|---|---|---|
| No. 1 + (A) | 40 + 40 | 100 | 93 |
| No. 1 + (A) + (B) | 40 + 20 + 20 | 100 | 100 |
| No. 2 + (A) | 40 + 40 | 100 | 93 |
| No. 3 + (A) | 40 + 40 | 100 | 97 |
| No. 4 + (A) | 40 + 40 | 100 | 100 |
| No. 4 + (A) + (B) | 40 + 20 + 20 | 100 | 100 |
| No. 5 + (A) | 40 + 40 | 100 | 93 |
| No. 5 + (A) + (B) | 40 + 20 + 20 | 100 | 100 |
| No. 1 | 40 | 100 | 0 |
| No. 2 | 40 | 100 | 0 |
| No. 3 | 40 | 100 | 0 |
| No. 4 | 40 | 100 | 0 |
| No. 5 | 40 | 100 | 0 |
| (A) | 40 | 0 | 60 |
| (B) | 40 | 0 | 90 |
| Non-treated | — | 0 | 0 |

Note

1. None of the mixtures and single compounds used in Example 1, (1) and (2) were seen to cause phytotoxicity.
2. Compounds of general formula (I) used in EXAMPLE 1

Compound No. 1
1-(2-methyl-5-pyridylmethyl)-2-(nitromethylene)tetrahydropyrimidine
Compound No. 2
1-(2-methoxy-5-pyridylmethyl)-2-(nitromethylene)tetrahydropyrimidine
Compound No. 3
1-(2-bromo-5-pyridylmethyl)-2-(nitromethylene)tetrahydropyrimidine
Compound No. 4
1-(2-chloro-5-pyridylmethyl)-2-(nitromethylene)imidazoline
Compound No. 5
1-(2-fluoro-5-pyridylmethyl)-2-(nitromethylene)imidazolidine 3. Compounds used in the invention
Compound (A): edifenphos
Compound (B) phthalide

EXAMPLE 2

When the active substance combinations used in Example 1 were applied to test areas where brown planthoppers and rice blast occurred simultaneously, the insects and the disease could be completely controlled accurately at the same time with a control index of 100%.

EXAMPLE 3 (Wettable powder)

Twenty five parts of active compound of formula (I), 25 parts of edifenphos, 45 parts of a 1:5 mixture of powdery diatomaceous earth and powder clay, 2 parts of sodium alkylbenzenesulfonate, and 3 parts of a sodium alkylnaphthalenesulfonate/formaldehyde condensate are pulverized and mixed to form a wettable powder.

EXAMPLE 4 (Dust)

One part of active compound of formula (I), 2 parts of edifenphos and 97 parts of weight of powdery clay are pulverized and mixed to form a dust.

(B) Biological and Formulation Examples relating to novel substance combinations of (1) a nitromethylene derivative of formula (I) and (3) the compound 4, 5, 6, 7-tetrachlorophthalide.

EXAMPLE 5

(1) Test of brown planthopper (Nilaparvata lugens):
Preparation of test compounds
Each active compound: 25 to 50 parts by weight
Carrier: 45 to 70 parts by weight of a 1:5 mixture of diatomaceous earth and kaolin
Emulsifier: 5 parts by weight of polyoxyethylene alkyl phenyl ether The active compound, the carrier and the emulsifier in the amounts indicated above were pulverized and mixed to form each wettable powder. A predetermined amount of said wettable powder was diluted with water and mixed.

Testing method

Three rice seedlings, 15 cm tall, were planted in each of pots having a diameter of about 13 cm. Ten days after the planting a water dilution of the active compounds in a predetermined concentration prepared in advance was sprayed onto the plants at a rate of 20 ml per pot by means of a spray gun. After having air dried the spray, a cage was put over each pot, and ten 4th instar larvae of brown planthopper were inoculated in each pot. Three days later, the number of dead insects was counted, and the kill ratio was calculated.

(2) Test for efficacy on rice blast by foliar application:

Testing method

Paddy rice (variety: Asahi) was grown in unglazed pots each having a diameter of 12 cm, and in the 3- to 4-leaf stage, a dilution of the active compounds in a predetermined concentration prepared in advance was sprayed onto the plants at a rate of 50 ml per three pots. On the next day, an artificially cultivated suspension of *Piricularia oryzae* spores was inoculated in the plants by spraying it twice. The pots were then maintained in a chamber kept at 25° C. and a relative humidity of 100% to cause infection. Seven days after the inoculation, the degree of disease per pot was rated and evaluated on the following standards and the control index (%) was calculated. The phytotoxicity to the plant was also examined.

| Degree of disease | Percentage of the area of lesions |
|---|---|
| 0 | 0 |
| 0.5 | 2 or less |
| 1 | 3–5 |
| 2 | 6–10 |
| 3 | 11–20 |
| 4 | 21–40 |
| 5 | 41 or more |

$$\text{Control index (\%)} = \frac{\text{Degree of disease in the non-treated area} - \text{Degree of disease in the treated area}}{\text{Degree of disease in the non-treated area}} \times 100$$

In the present tests, one test area consisted of three pots.

The results of the test (1) and (2) are summarized in Table 2.

TABLE 2

| Test chemical | Concentrations of the active ingredients (ppm) | Efficacy Kill ratio (% of brown) plant-hopper | Efficacy Control index (%) of rice blast |
|---|---|---|---|
| No. 1 + (B) | 40 + 40 | 100 | 97 |
| No. 2 + (B) | 40 + 40 | 100 | 97 |
| No. 3 + (B) | 40 + 40 | 100 | 100 |
| No. 4 + (B) | 40 + 40 | 100 | 100 |
| No. 5 + (B) | 40 + 40 | 100 | 93 |
| No. 1 | 40 | 100 | 0 |
| No. 2 | 40 | 100 | 0 |
| No. 3 | 40 | 100 | 0 |
| No. 4 | 40 | 100 | 0 |
| No. 5 | 40 | 100 | 0 |
| (B) | 40 | 0 | 90 |
| Non-treated | | 0 | 0 |

Note

1. None of the mixtures and single compounds used in Example 5, (1) and (2) were seen to cause phytotoxicity.
2. Compounds of general formula (I) used in the invention Compound No. 1
1-(2-methyl-5-pyridylmethyl)-2-(nitromethylene)tetrahydropyrimidine Compound No. 2
1-(2-methoxy-5-pyridylmethyl)-2-(nitromethylene)tetrahydropyrimidine Compound No. 3
1-(2-bromo-5-pyridylmethyl)-2-(nitromethylene)tetrahydropyrimidine Compound No. 4
1-(2-chloro-5-pyridylmethyl)-2-(nitromethylene)imidazolidine Compound No. 5
1-(2-fluoro-5-pyridylmethyl)-2-(nitromethylene)imidazolidine 3. Compounds used in the invention
Compound (B): phthalide

EXAMPLE 6

When the active substance combinations used in Example 5 were applied to test areas where brown planthoppers and rice blast occurred simultaneously, the insects and the disease could be completely controlled accurately at the same time with a control index of 100%.

EXAMPLE 7 (Wettable powder)

Twenty five parts of active compound of formula (I), 25 parts of phthalide, 45 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder.

EXAMPLE 8 (Dust)

One part of active compound of formula (I), 2.5 parts of phthalide and 96.5 parts of weight of powdery clay are pulverized and mixed to form a dust.

(C) Biological and Formulation Examples relating to novel substance combinations of (1) a nitromethylene derivative of formula (I) and (4) 1-(4-chlorobenzyl)-1-cyclopentyl-3-phenylurea:

EXAMPLE 9

(1) Test on brown planthopper (*Nilaparvata lugens*):
Preparation of test compounds
Each active compound: 25 parts by weight
Carrier: 70 parts by weight of a 1:5 mixture of diatomaceous earth and kaolin
Emulsifier: 5 parts by weight of polyoxyethylene alkyl phenyl ether The active compound, the carrier and the emulsifier in the amounts indicated above were pulverized and mixed to form each wettable powder. A predetermined amount of said wettable powder was diluted with water and mixed.

Testing method

Three rice seedlings, 15 cm tall, were planted in pots having a diameter of about 13 cm. Ten days after the planting a water dilution of the active compounds in a predetermined concentration prepared in advance was sprayed onto the plants at a rate of 20 ml per pot by means of a spray gun. After having air dried the spray, a cage was put over each pot, and ten 4th instar larvae of brown planthopper were inoculatd in each pot. Three days later, the number of dead insects was counted, and the kill ratio was calculated.

(2) Test for controlling efficacy on rice sheath blight:

Testing method

Rice (variety: Kinmaze) was cultivated in Wagner pots (1a/5000) in the submerged state, and in its early earforming stage, a dilution of the active compounds in a predetermined concentration prepared in advance was sprayed onto the plant at a rate of 100 ml per 3 pots.

On the day after spraying, *Pellicularia sasakii* which had been cultivated for 10 days in barley medium to the stage of sclerotium formation was inoculated in the root portion of the rice plants. The pots were maintained for 10 days in a chamber kept at a temperature of 28° to 30° C. and a relative humidity of at least 95% to induce start of disease. Thereafter, the degree of disease and the phytotoxicity were examined. The growth of the lesion from the inoculated part of the root portion was examined, and the degree of damage was expressed on the following standards. The control index was also calculated.

$$\text{Degree of damage} = \frac{2n_3 + 2n_2 + n_1 + n_0}{3N} \times 100$$

where
- N: the total number of culms examined
- $n_0$: the number of culms not diseased
- $n_1$: the number of culms diseased up to the first leaf sheath from the bottom
- $n_2$: the number of culms diseased up to the second leaf sheath from the bottom
- $n_3$: the number of culms diseased up to the third leaf sheath from the bottom or higher.

The results obtained in tests (1) and (2) are summarized in Table 3.

TABLE 3

| | | Efficacy | |
|---|---|---|---|
| Test chemical | Concentrations of the active ingredients (ppm) | Kill ratio (%) of brown plant-hopper | Control index (%) of rice sheath blight |
| No. 1 + (C) | 40 + 20 | 100 | 100 |
| No. 2 + (C) | 40 + 20 | 100 | 100 |
| No. 3 + (C) | 40 + 20 | 100 | 100 |
| No. 4 + (C) | 40 + 20 | 100 | 100 |
| No. 5 + (C) | 40 + 20 | 100 | 100 |
| No. 1 | 40 | 100 | 0 |
| No. 2 | 40 | 100 | 0 |
| No. 3 | 40 | 100 | 0 |
| No. 4 | 40 | 100 | 0 |
| No. 5 | 40 | 100 | 0 |
| (C) | 20 | 0 | 80 |
| Non-treated | | 0 | 0 |

Note
1. None of the mixtures and single compounds used in Example 9 caused phytotoxicity.
2. Compounds of general formula (I) used in the invention Compound No. 1
1-(2-methyl-5-pyridylmethyl)-2-(nitromethylene)tetrahydropyrimidine Compound No. 2
1-(2-methoxy-5-pyridylmethyl)-2-(nitromethylene)tetrahydropyrimidine Compound No. 3
1-(2-bromo-5-pyridylmethyl)-2-(nitromethylene)tetrahydropyrimidine Compound No. 4
1-(2-chloro-5-pyridylmethyl)-2-(nitromethylene)imidazolidine Compound No. 5
1-(2-fluoro-5-pyridylmethyl)-2-(nitromethylene)imidazolidine 3. Compound used in the invention
Compound (C): pencycuron

EXAMPLE 10

When the active substance combinations used in Example 9 were applied to test areas where brown planthoppers and rice sheath blight occurred simultaneously, the insects and the disease could be completely controlled accurately at the same time with a control index of 100%.

EXAMPLE 11 (Wettable powder)

Twenty five parts of active compound of formula (I), 25 parts of pencycuron, 45 parts of a 1:5 mixture of powdery diatomaceous earth and powder clay, 2 parts of sodium alkylbenzenesulfonate, and 3 parts of a sodium alkylnaphthalenesulfonate/formaldehyde condensate are pulverized and mixed to form a wettable powder.

EXAMPLE 12 (Dust)

One part of active compound of formula (I), 1.5 parts of pencycuron and 97.5 parts of weight of powdery clay are pulverized and mixed to form a dust.

(D) Biological and Formulation Examples relating to novel substance combinations of (1) a nitromethylene derivative of formula (I) and a compound of group (5):

EXAMPLE 13

(1) Test of brown planthopper (*Nilaparvata lugens*):
Preparation of test compounds
Each active compound: 25 parts by weight
Carrier: 70 parts by weight of a 1:5 mixture of diatomaceous earth and kaolin
Emulsifier: 5 parts by weight of polyoxyethylene alkyl phenyl ether The active compound, the carrier and the emulsifier in the amounts indicated above were pulverized and mixed to form each wettable powder. A predetermined amount of said wettable powder was diluted with water and mixed.

Testing method

Three rice seedlings, 15 cm tall, were planted in pots having a diameter of about 13 cm. Ten days after the planting a water dilution of the active compounds in a predetermined concentration prepared in advance was sprayed onto the plants at a rate of 20 ml per pot by means of a spray gun. After having air dried the spray, a cage was put over each pot, and ten 4th instar larvae of brown planthopper were inoculated in each pot. Three days later, the number of dead insects was counted, and the kill ratio was calculated.

(2) Test for controlling efficacy on rice sheath blight

Testing method

Rice (variety: Kinmaze) was cultivated in Wagner pots (1a/5000) in the submerged state, and in its early earforming stage, a dilution of the active compounds in a predetermined concentration prepared in advance was sprayed onto the plant at a rate of 100 ml per 3 pots.

On the day following the day of spraying, *Pellicularia sasakii* which had been cultivated for 10 days in a barley medium to the stage of sclerotium formation were inoculated in the root portion of the rice plants. The pots were maintained for 10 days in a chamber kept at a temperature of 28° to 30° C. and a relative humidity of at least 95% to induce start of disease. Thereafter, the degree of disease and the phytotoxicity were examined. The growth of the lesion from the inoculated part of the root portion was examined, and the degree of damage was expressed by means of the following standard. The control index was also calculated.

$$\text{Degree of damage} = \frac{2n_3 + 2n_2 + n_1 + n_0}{3N} \times 100$$

where
N: the total number of culms examined
$n_0$: the number of culms not diseased
$n_1$: the number of culms diseased up to the first leaf sheath from the bottom
$n_2$: the number of culms diseased up to the second leaf sheath from the bottom
$n_3$: the number of culms diseased up to the third leaf sheath from the bottom or higher.

The results obtained in tests (1) and (2) are summarized in Table 4.

TABLE 4

| Test chemical | Concentration of the active ingredients (ppm) | Efficacy Kill ratio (%) of brown plant-hopper | Control index (%) of rice sheath blight |
| --- | --- | --- | --- |
| No. 1 + (D) | 40 + 30 | 100 | 97 |
| No. 1 + (E) | 40 + 80 | 100 | 95 |
| No. 2 + (D) | 40 + 30 | 100 | 98 |
| No. 2 + (E) | 40 + 80 | 100 | 92 |
| No. 3 + (D) | 40 + 30 | 100 | 97 |
| No. 3 + (E) | 40 + 80 | 100 | 97 |
| No. 4 + (D) | 40 + 30 | 100 | 100 |
| No. 4 + (E) | 40 + 80 | 100 | 99 |
| No. 5 + (D) | 40 + 30 | 100 | 100 |
| No. 5 + (E) | 40 + 80 | 100 | 99 |
| No. 1 | 40 | 100 | 0 |
| No. 2 | 40 | 100 | 0 |
| No. 3 | 40 | 100 | 0 |
| No. 4 | 40 | 100 | 0 |
| No. 5 | 40 | 100 | 0 |
| (D) | 30 | 0 | 90 |
| (E) | 80 | 0 | 90 |
| Non-treated | — | 0 | 0 |

Note

1. None of the mixtures and single compounds used in Example 13, (1) and (2) caused phytotoxicity.

2. Compounds of general formula (I) used in the invention.
Compound No. 1
1-(2-methyl-5-pyridylmethyl)-2-(nitromethylene)tetrahydropyrimidine
Compound No. 2
1-(2-methoxy-5-pyridylmethyl)-2-(nitromethylene)tetrahydropyrimidine
Compound No. 3
1-(2-bromo-5-pyridylmethyl)-2-(nitromethylene)tetrahydropyrimidine
Compound No. 4
1-(2-chloro-5-pyridylmethyl)-2-(nitromethylene)imidazolidine
Compound No. 5
1-(2-fluoro-5-pyridylmethyl)-2-(nitromethylene)imidazolidine 3. Compound used in the invention
Compound (D): Validamycin A
Compound (E): flutolanil (tradename: Moncut ®)

EXAMPLE 14

When the active substance combinations used in Example 13 were applied to test areas where brown planthoppers and rice sheath blight occurred simultaneously, the insects and the disease could be completely controlled accurately at the same time with a control index of 100%.

EXAMPLE 15 (Wettable powder)

Twenty five parts of active compound of formula (I), 25 parts of flutolanil, 45 parts of a 1:5 mixture of powdery diatomaceous earth and powder clay, 2 parts of sodium alkylbenzenesulfonate, and 3 parts of a sodium alkylnaphthalenesulfonate/formaldehyde condensate are pulverized and mixed to form a wettable powder.

EXAMPLE 16 (Dust)

One part of active compound of formula (I), 1.5 parts of flutolanil and 97.5 parts of weight of powdery clay are pulverized and mixed to form a dust.

(E) Biological and Formulation Examples relating to novel substance combinations of (1) a nitromethylene derivative of formula (I) and a compound of group (6):

EXAMPLE 17

Test for efficacy by water surface application:
Preparation of test compounds
Each active compound: 5 to 25 parts by weight
Carrier: 70 to 90 parts by weight of a 1:5 mixture of diatomaceous earth and kaolin
Emulsifier: 5 parts by weight of polyoxyethylene alkyl phenyl ether The active compound, the carrier and the emulsifier in the amounts indicated above were pulverized and mixed to form each wettable powder. A predetermined amount of said wettable powder was diluted with water and mixed.

Testing method

Rice plants (variety: Asahi) were planted in white porcelain pots having a diameter of 12 cm at a rate of three stocks, and grown in the submerged state. In the early stage of their tillering, each of the chemicals in a predetermined concentration prepared in advance was poured onto the water surface in the amounts indicated with care taken not to apply it directly to the overground portions of the rice plants. Three days later, cages were put over the pots, and 4th instar larvae of brown planthopper (Nilaparvata lugens) were inoculated at a rate of 10 heads per pot. Two days after the inoculation, the number of dead insects was counted, and the kill ratio was calculated.

Thereafter, by a customary method, suspension of spores of Piricularia oryzae was sprayed over the plants, and the pots were maintained for 24 hours in an incubator kept at a temperature of 23° to 25° C. and a relative humidity of 100%, and thereafter transferred to a glass greenhouse kept at a temperature of 20° to 28° C. Seven days after the inoculation, the degree of disease per pot was rated and evaluated on the following standard, and the control index (%) was calculated. The phytotoxicity was examined at the same time.

| Degree of disease | Percentage of the area of lesions |
| --- | --- |
| 0 | 0 |

-continued

| Degree of disease | Percentage of the area of lesions |
|---|---|
| 0.5 | 2 or less |
| 1 | 3–5 |
| 2 | 6–10 |
| 3 | 11–20 |
| 4 | 21–40 |
| 5 | 41 or more |

$$\text{Control index (\%)} = \frac{\text{Degree of disease in the non-treated area} - \text{Degree of disease in the treated area}}{\text{Degree of disease in the non-treated area}} \times 100$$

In the present tests, one test area consisted of three pots.

The results of tests (1) and (2) are summarized in Table 5.

TABLE 5

| Test chemical | Concentration of the active ingredients (ppm) | Effect Kill ratio (%) of brown plant-hopper | Control index (%) of rice blast |
|---|---|---|---|
| No. 1 + (F) | 1 + 2 | 100 | 100 |
| No. 1 + (G) | 1 + 3 | 100 | 97 |
| No. 2 + (F) | 1 + 2 | 100 | 100 |
| No. 2 + (G) | 1 + 3 | 100 | 93 |
| No. 3 + (F) | 1 + 2 | 100 | 100 |
| No. 3 + (G) | 1 + 3 | 100 | 97 |
| No. 4 + (F) | 1 + 2 | 100 | 100 |
| No. 4 + (G) | 1 + 3 | 100 | 100 |
| No. 5 + (F) | 1 + 2 | 100 | 100 |
| No. 5 + (G) | 1 + 3 | 100 | 100 |
| No. 1 | 1 | 100 | 0 |
| No. 2 | 1 | 100 | 0 |
| No. 3 | 1 | 100 | 0 |
| No. 4 | 1 | 100 | 0 |
| No. 5 | 1 | 100 | 0 |
| (F) | 2 | 0 | 100 |
| (G) | 3 | 0 | 93 |
| Non-treated | — | 0 | 0 |

Note
1. None of the mixtures and single compounds used in Example 17 were seen to cause phytotoxicity.
2. Compounds of general formula (I) used in the invention
 Compound No. 1
 1-(2-methyl-5-pyridylmethyl)-2-(nitromethylene)tetrahydropyrimidine
 Compound No. 2
 1-(2-methoxy-5-pyridylmethyl)-2-(nitromethylene)tetrahydropyrimidine
 Compound No. 3
 1-(2-bromo-5-pyridylmethyl)-2-(nitromethylene)tetrahydropyrimidine
 Compound No. 4
 1-(2-chloro-5-pyridylmethyl)-2-(nitromethylene)imidazolidine
 Compound No. 5
 1-(2-fluoro-5-pyridylmethyl)-2-(nitromethylene)imidazolidine
3. Compound used in the invention
 Compound (F): pyroquilon
 Compound (G): probenazole

EXAMPLE 18

Test for efficacy by application to a nursery box:
Preparation of test compounds Water (25 parts) is added to a mixture consisting of 5 (or 4) parts of active compound, 30 parts of bentonite (montmorillonite), 63 (or 64) parts of talc and 2 parts of a lignosulfonate, and they are well kneaded. The mixture is processed by an extrusion-type granulating machine to form granules having a size of 10 to 40 mesh which are then dried at 40° to 50° C. to form granules.

Rice seedlings were grown in seedling nursing boxes (30 cm × 60 cm × 2 cm), and 21 days after emergence, 50 g per box of granules of the active compound of general formula (I) (6%) and 50 g per box of granules of tricyclazole (4%) were uniformly applied. After the application, three rice seedlings were pulled up together with the soil from each pot and transplanted in a pot (1/10000a) in a greenhouse. Three days after transplantation, a plastic cage was put over each pot, and ten 4th instar larvae of brown planthopper (Nilaparavata lugens) were released into the cage. Two days later, the number of dead insects was counted, and the kill ratio was calculated.

Twenty days after the transplantation when the seedlings set and grew well, a suspension of spores of Piricularia oryzae was sprayed over the plants by a customary method, and the pots were maintained for 24 hours in an incubator kept at a temperature of 23° to 25° C. and a relative humidity of 100%, and thereafter transferred to a glass greenhouse kept at a temperature of 20° to 28° C. Seven days after the inoculation, the degree of disease per pot was rated and evaluated on the following standard, and the control index (%) was calculated. The phytotoxicity was examined at the same time.

| Degree of disease | Percentage of the area of lesions |
|---|---|
| 0 | 0 |
| 0.5 | 2 or less |
| 1 | 3–5 |
| 2 | 6–10 |
| 3 | 11–20 |
| 4 | 21–40 |
| 5 | 41 or more |

The results are shown in Table 6.

TABLE 6

| Test chemical | Concentration of the active ingredients (ppm) | Effect Kill ratio (%) of brown plant-hopper | Control index (%) of rice blast |
|---|---|---|---|
| No. 1 + (H) | 3 + 2 | 100 | 97 |
| No. 2 + (H) | 3 + 2 | 100 | 97 |
| No. 3 + (H) | 3 + 2 | 100 | 93 |
| No. 4 + (H) | 3 + 2 | 100 | 100 |
| No. 5 + (H) | 3 + 2 | 100 | 100 |
| No. 1 | 3 | 100 | 0 |
| No. 2 | 3 | 100 | 0 |
| No. 3 | 3 | 100 | 0 |
| No. 4 | 3 | 100 | 0 |
| No. 5 | 3 | 100 | 0 |
| (H) | 2 | 0 | 93 |
| Non-treated | — | 0 | 0 |

Note

1. None of the mixtures and single compounds used in Example 2 were seen to cause phytotoxicity.
2. Compounds of general formula (I) used in the invention Compounds Nos. (1), (2), (3), (4) and (5) are the same as those described in Example 17.

3. Compound used in the invention
Compound (H): tricyclazole

EXAMPLE 18

(1) Test on brown planthopper (*Nilaparvata lugens*):
Preparation of test compounds
Each active compound: 30 to 40 parts by weight
Carrier: 5 to 65 parts by weight of a 1:5 mixture of diatomaceous earth and kaolin
Emulsifier: 5 parts by weight of polyoxyethylene alkyl phenyl ether The active compound, the carrier and the emulsifier in the amounts indicated above were pulverized and mixed to form each wettable powder. A predetermined amount of said wettable powder was diluted with water and mixed.

Testing method

Three rice seedlings, 15 cm tall, were planted in each of pots having a diameter of about 13 cm. Ten days after the planting a water dilution of the active compounds in a predetermined concentration prepared in advance was sprayed onto the plants at a rate of 20 ml per pot by means of a spray gun. After air drying the spray, a cage was put over each pot, and ten 4th instar larvae of brown planthopper were inoculated in each pot. Three days later, the number of dead insects were counted, and the kill ratio was calculated.

(2) Test for efficacy on rice blast by foliar application

Testing method

Paddy rice (variety: Asahi) was grown in unglazed pots each having a diameter of 12 cm, and in the 3- to 4-leaf stage, a dilution of the active compounds in a predetermined concentration prepared in advance was sprayed onto the plants at a rate of 50 ml per three pots. On the next day, an artificially cultivated suspension of *Piricularia oryzae* spores was inoculated in the plants by spraying it twice. The pots were then maintained in a chamber kept at 25° C. and a relative humidity of 100% to cause infection. Seven days after the inoculation, the degree of desease per pot was rated and evaluated on the following standard, and the control index (%) was calculated. The phytotoxicity to the plants was also examined.

| Degree of disease | Percentage of the area of lesions |
|---|---|
| 0 | 0 |
| 0.5 | 2 or less |
| 1 | 3–5 |
| 2 | 6–10 |
| 3 | 11–20 |
| 4 | 21–40 |
| 5 | 41 or more |

$$\text{Control index (\%)} = \frac{\begin{array}{c}\text{Degree of} \\ \text{disease in} \\ \text{the non-} \\ \text{treated area}\end{array} - \begin{array}{c}\text{Degree of} \\ \text{disease in} \\ \text{the treated} \\ \text{area}\end{array}}{\text{Degree of disease in the non-treated area}} \times 100$$

In the present tests, one test area consisted of three pots.

The results of tests (1) and (2) are summarized in Table 7.

TABLE 7

| Test chemical | Concentration of the active ingredients (ppm) | Efficacy Brown plant-hopper Kill ratio (%) | Rice blast Control index (%) |
|---|---|---|---|
| No. 1 + (I) | 40 + 50 | 100 | 90 |
| No. 2 + (I) | 40 + 50 | 100 | 90 |
| No. 3 + (I) | 40 + 50 | 100 | 90 |
| No. 4 + (I) | 40 + 50 | 100 | 93 |
| No. 5 + (I) | 40 + 50 | 100 | 93 |
| No. 1 | 40 | 100 | 0 |
| No. 2 | 40 | 100 | 0 |
| No. 3 | 40 | 100 | 0 |
| No. 4 | 40 | 100 | 0 |
| No. 5 | 40 | 100 | 0 |
| (I) | 50 | 0 | 67 |
| Non-treated | — | 0 | 0 |

Note

1. None of the mixtures and single compounds used in Example 3 were seen to cause phytotoxicity.
2. Compounds of general formula (I) used in the invention Compounds No. (1), (2), (3), (4) and (5) are the same as those described in Example 17.

3. Compound used in the invention
Compound (I): isoprothiolane

EXAMPLE 19

When the active compound mixtures used in Example 18 were applied to test area where brown planthoppers and rice blast occurred simultaneously, the insects and the disease could be completely controlled accurately at the same time.

EXAMPLE 20 (Wettable powder)

Twenty five parts of active compound of formula (I), 25 parts of isoprothiolane, 45 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder.

EXAMPLE 21 (Granules)

Water (25 parts) is added to a mixture consisting of 3 parts of active compound of formula (I), 8 parts of probenazole, 30 parts of bentonite (montmorillonite), 57 parts of talc and 2 parts of a lignosulfonate, and they are well kneaded. The mixture is processed by an extrusion-type granulating machine to form granules having a size of 10 to 40 mesh which are then dried at 40° to 50° C. to form granules.

EXAMPLE 22 (Dust)

One part of active compound of formula (I), 2.5 parts of isoprothiolane and 96.5 parts of weight of powdery clay are pulverized and mixed to form a dust.

It is understood that the specification and examples are illustrative but not limitative of the present invention and that other embodiments within the spirit and scope of the invention will suggest themselves to those skilled in the art.

We claim:

1. An insecticidally and fungicidal composition comprising
   (A) (1) n insecticidally effective amount of a nitromethylbenzanilide derivative of the formula

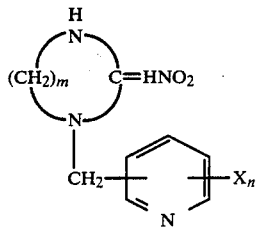

in which
   X is a lower alkyl group, a lower alkoxy group, or a halogen atom,
   n is 0, 1 or 2, and
   m is 2 or 3, and
   (B) a fungicidally effective amount of at least one fungicide selected from the group consisting of
   (2) O-ethyl S,S-diphenyl phosphorodithioate,
   (3) 4,5,6,7-tetrachlorophthalide,
   (4) 1-(4-chlorobenzyl)-1-cyclopentyl-3-phenylurea,
   (5) Validamycin A, 3'-iso-propoxy-2-methylbenzenilide, o-trifluoromethyl-m'-isopropoxybenzoylanilide or 6-(3,5-dichloro-4-methylphenyl-3(2H)pyridazinone, and
   (6) di-isopropyl-1,3-dithiolan-2-ylidenemalonate, 5-methyl-1,2,4-triazo[3,4-b]-benzothiazole, 3-allyloxy-1,2-benzisothiazole 1,1-dioxide, and 1,2,5,6-tetrahydro-4H-pyrrolo-]3,2,1-i,j]quinolin-4-one, (5-amino-2-methyl-6-(2,3,4,5,6-pentahydroxycyclohexyloxy)tetrahydropyran-3-yl]amino-$\alpha$-iminoacetic acid or S-benzyl diisopropylphosphorothilate.

2. A composition according to claim 1, wherein (B) is O-ethyl, S,S-diphenyl phosphorodithioate.

3. A composition according to claim 1, wherein (B) is 1-(4-chlorobenzyl)-1-cyclopentyl-3-phenylurea.

4. A composition according to claim 1, wherein (B) is di-isopropyl 1,3-dithiolan-2-ylidenemalonate.

5. An insecticidal and fungicidal composition according to claim 1, wherein the weight ratio of (A):(B) is between 1:0.05 and 1:20.

6. A composition according to claim 1, in which
   X is methyl, methoxy, chlorine, bromine or fluorine,
   n is 1 or 2,
   m is 2 or 3, and
   the CH$_2$ moiety is bonded to the 3- or 5-position of the pyridine ring.

7. A method of combating insects and fungi which comprises applying thereto or to a habitat thereof an insecticidally and fungicidally effective amount of a composition according to claim 1.

* * * * *